United States Patent [19]
Carroll

[11] Patent Number: 4,475,481
[45] Date of Patent: Oct. 9, 1984

[54] IDENTIFICATION SYSTEM

[75] Inventor: Gary T. Carroll, Boulder, Colo.

[73] Assignee: B.I. Incorporated, Boulder, Colo.

[21] Appl. No.: 437,841

[22] Filed: Oct. 29, 1982

Related U.S. Application Data

[63] Continuation-in-part of Ser. No. 280,341, Jul. 6, 1981, abandoned.

[51] Int. Cl.³ ................................................ A01K 5/02
[52] U.S. Cl. .................................................. 119/51 R
[58] Field of Search ................. 119/51 R; 340/825.54; 343/6.5 SS

[56] References Cited

U.S. PATENT DOCUMENTS

| | | | |
|---|---|---|---|
| 3,465,724 | 9/1969 | Broadbent | 119/51 R |
| 3,516,575 | 6/1970 | Moffitt | 222/52 |
| 3,541,995 | 11/1970 | Fathauer | 119/51 R |
| 3,557,758 | 1/1971 | Lack | 119/51 R |
| 4,129,855 | 12/1978 | Rodrian | 340/825.54 |
| 4,196,418 | 4/1980 | Kip et al. | 343/6.5 SS X |
| 4,262,632 | 4/1981 | Hanton et al. | 119/1 |
| 4,274,083 | 6/1981 | Tomoeda | 119/51 R X |

Primary Examiner—Hugh R. Chamblee
Attorney, Agent, or Firm—Bryant R. Gold

[57] ABSTRACT

An identification system comprising an intermittent electromagnetic generator at one frequency and a remote receiver for receiving the electromagnetic energy and using it to power an encoder of digital information and a transmitter at a different frequency for transmitting the encoder digital information and a receiver remote from said transmitter for decoding and comparing the decoded digital data with stored data to initiate commands for functions such as feeding, ration dispensing, and the like in response to the predetermined comparison criteria of decoded data and such stored data.

18 Claims, 10 Drawing Figures

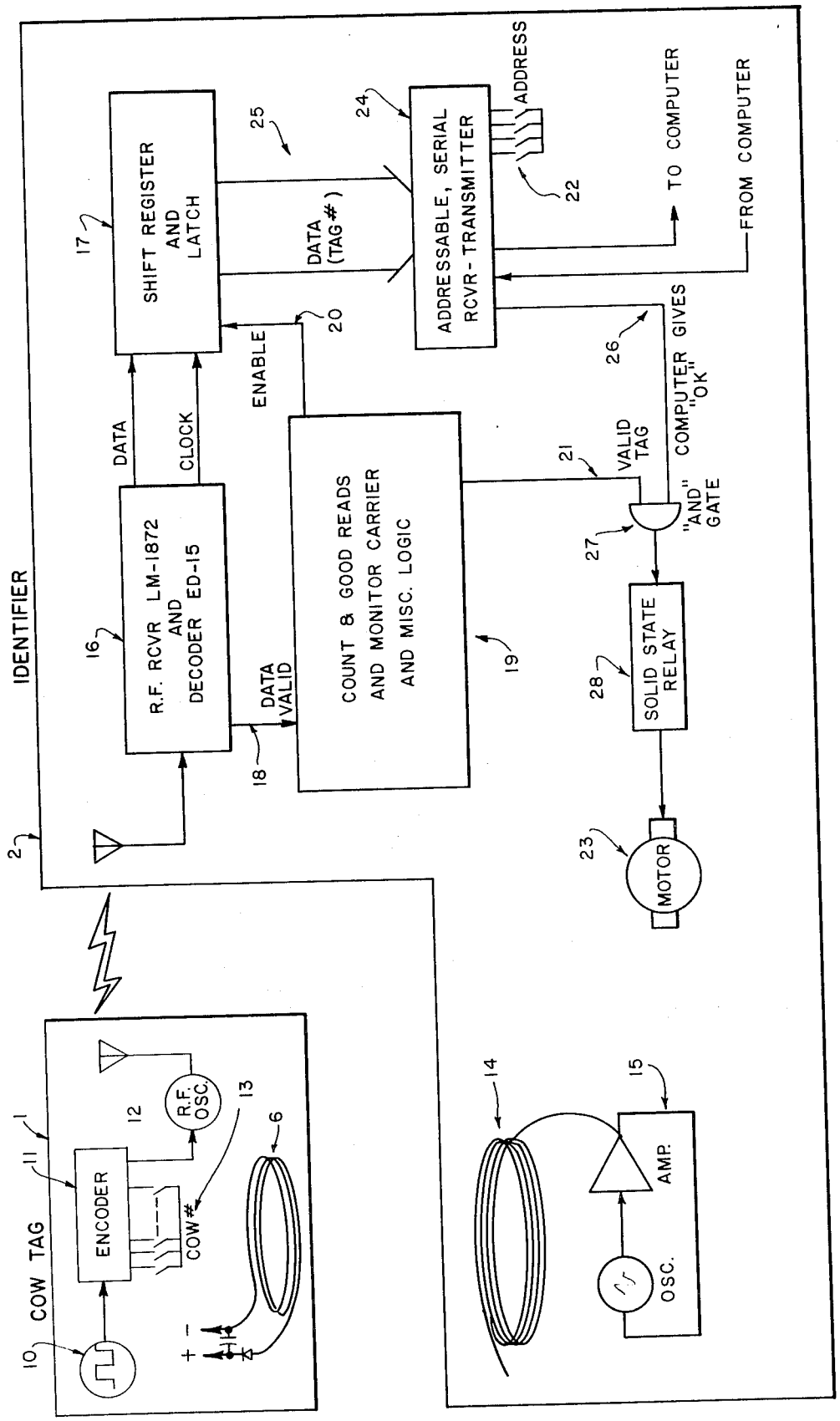

IDENTIFICATION SYSTEM

CROSS REFERENCE TO RELATED APPLICATIONS

This application is a continuation-in-part of application Ser. No. 280,341, filed 07/06/81, now abandoned.

FIELD OF THE INVENTION

The present invention relates to an electronic device capable of being used in an identification system and more particularly to identifying moveable objects.

The field of identification has in the past employed transponder devices which are either implanted in the case of animals or incorporated in tags or the like but have generally relied upon either self-contained power supplies and have required line of sight transponders. These have suffered from several drawbacks including limited life, high maintenance and the like and have therefore had limited utility particularly in situations where it is inconvenient or impractical to replace the batteries in the transponder units.

In the environment of animal identification, it is important to identify dairy cows, beef cattle, pigs, sheep, and other producing stock in order to monitor over-all herd or flock performance as well as being able to identify and measure the performance of individuals. This is particularly important in the dairy industry.

To increase the productivity of dairy cows, each animal has to be individually fed according to her age, health and lactation stage, thus a means of identification is needed so each and every cow can be taken care of individually according to several parameters.

In the past, all animals were fed approximately the same amount, which meant the poor producers were overfed and the potential high producers could be underfed thus wasting expensive feed and resulting in a lower overall milk production. Several approaches to the solution of this problem have been attempted to enable more cost effective herd management.

The use of modern electronic technology has begun to be used to achieve the desired increased efficiency. In the case of animal identification, the identification of individual animals through the use of a passive transponder worn around the neck allows each animal to be identified and fed according to her own age, health, position on her lactation curve, and even milk production data.

Systems of this type have been developed; but cost, size and lack of electrical noise immunity have been a major drawback. The system of the present invention includes in one form a low cost passive electronic tag device or transponder which when close to an identifier is capable of communicating with a high signal-to-noise ratio, as well as with good discrimination between its signal and those signals from the tags of animals not immediately proximate to the identifier of the system.

SUMMARY OF THE INVENTION

Specifically, the present invention can be practiced by providing a self-resonating power oscillator driven coil operating at one frequency to create an electromagnetic field. This power oscillator device in the system of the present invention is referred to as an identifier. In its preferred form, it utilizes an intermittent field which pulses in a predetermined manner to charge a storage device in a remote passive pulsed electronic identification circuit when that circuit is present in the electromagnetic field generated by the identifier. The identifier is also provided with a receiver which is activated between the electromagnetic pulses for receiving an R.F. signal that is generated by the passive electronic identification circuit when a predetermined amount of charge is provided to the circuit by the electromagnetic pulses of the identifier. Predetermined coded information in the form of a digital data stream is then transmitted back to the receiver of the identifier for subsequent processing in a central computer unit or remote unit or data process capability incorporated in the identifier in order to generate a functional signal enabling the activities of feeding by starting motors or other equipment for moving a specific feed ration or other activities related to the identification of a particular animal. Such functions could include gate operations for sorting or moving cattle, the initiation of a weighing function, a milk monitoring function or the like. Likewise, such an identification system has utility as an identification device for human security applications, access control or any other environments including hospitals, correctional institutions and other situations where positive electronic identification is desired or required.

In the case of feeding dairy cattle, a cow approaching a conventional feeder generally places her head into the feeder to eat the ration it contains. The passive electronic identification device when contained in a tag hanging from the cow's neck on a chain, falls into a position adjacent the front surface of the identifier. The electronic tag when powered up by its proximity to the identifier proceeds to generate a pre-programmed binary coded number, typically comprising a preamble followed by a unique animal identification number. The electronic tag then keys an RF oscillator that transmits this information in the manner described hereinafter to a receiver located in the identifier. This receiver converts the incoming RF signal into a standard digital bit stream that is sent to a decoder suitable circuit that converts this serial stream to a parallel binary coded number which is the same as the binary coded number pre-programmed inside the passive circuit in the electronic tag.

At the end of each burst of bits from the transmitter in the tag, the decoding device gives a signal called "data valid" that tells the system to latch (store) the parallel bits from the shift register so as to allow the Computer or other monitoring device to read these bits at any time.

From this parallel register the data can either be sent to an addressable UART, (Universal Asynchronous Receiver-Transmitter), that sends this information off to a central Computer through a three or four wire current loop interface in the ASCII standard communication format hereinafter called ASCII.

The UART in one embodiment is an addressable UART that has seven address lines allowing 127 of these addressable UARTS (identifiers) to be individually called and communicated with. The present invention uses only four of the lines providing for up to sixteen identifiers per system, all controlled by one main computer.

In an alternative embodiment of the invention, the identifier receiver sends its digital bit stream to a microcomputer device having coding and decoding capability such as an Intel 8085 or 8051 microcomputers. The microcomputer processes the data in a preprogrammed manner to produce signals for functions and- /or communication through a three or four wire current loop interface to a central computer in the same manner as the UART. In this embodiment, the microcomputer replaces the decoder circuit, shift registers, latches, "data valid" signal and UART employed in the other embodiment.

As previously described therefore, the ASCII data in the UART or microcomputer is transmitted to the central computer where it is converted to a tag number representative of a particular cow in the herd.

The central computer used will have been previously loaded by the operator with all the necessary data on each animal, including how much feed each animal is allowed to eat per day, responds to the tag number and decides if that particular animal is authorized to eat; and, if so, sends back an ASCII command response to the identifier.

The UART or microcomputer decoder at the identifier has an output that is "anded" with the equivalent of a "valid tag" signal and if both signals are present a relay is energized which turns on the AC motor mounted nearby in the feeder which then augers feed into the feeder whereby the animal can start to eat.

The motor runs at a known constant "pounds per second" rate and will continue to dispense feed until the computer gives a stop command. The animal then leaves the feeder allowing another animal to use the feeder, starting the whole process over with that new animal, i.e. identification, computer decision, computer command and feed ration dispensing.

The system can also be provided with a fail safe feature whereby a standard ration is dispensed into the feeder when the presence of a valid tag is sensed at the feeder even though the communications link with the central computer is inoperative.

BRIEF DESCRIPTION OF THE DRAWINGS

FIG. 3 is an electrical block diagram of the animal's Transponder, i.e. Tag.

FIG. 4 is an electrical block diagram of the identification system, i.e. identifier.

Appendix: a software appendix is included at the end of the specification.

DETAILED DESCRIPTION OF PREFERRED EMBODIMENTS OF THE INVENTION

Although the present invention may be found suitable for use in diverse identification applications, the preferred embodiment is particularly well adapted for use with dairy animals and will be specifically described in connection therewith.

Figure 1:
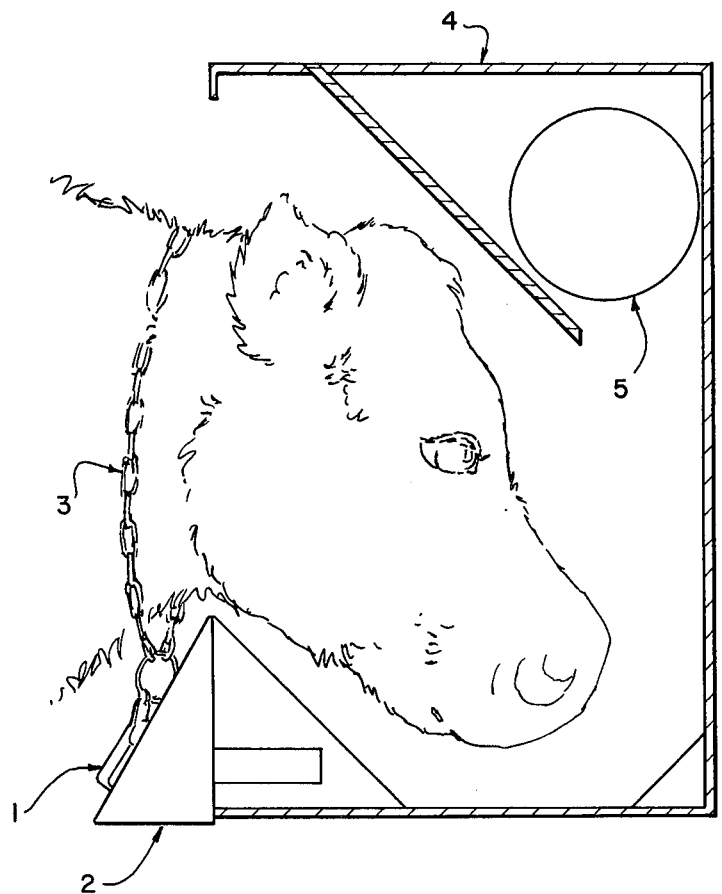
FIG. 1 is a pictorial view of the present invention applied to a cow.

As shown in FIG. 1, the basic system of the present invention involves the use of a transponder 1, worn around the neck of the animal by a chain or rope 3 and an identifier 2 that supplies power to the transponder and receives an RF signal generated by the transponder, decodes it and sends the information off to a computer where decisions are made on the information provided, and a computer generated command is sent back to operate the motor 5, which then augers the requisite amount of feed to the animal.

Each feeder box 4 has an identifier 2 mounted to it so that any animal with a transponder 1 can go to any feeder 4 and get fed that day's allotment of feed.

Figure 2:
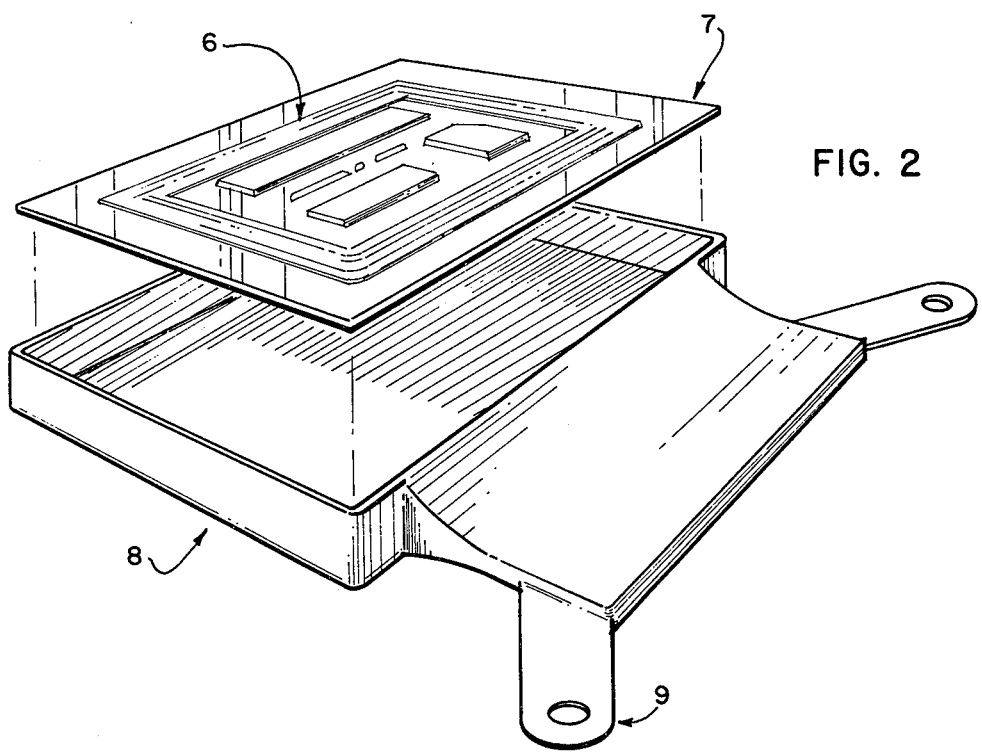
FIG. 2 is an exploded view of the Transponder unit which forms part of the present invention.

FIG. 2 shows an exploded view of the Transponder 1 including the power pick-up coil 6. This coil is analogous to the secondary of an air core transformer. FIG. 4 shows the identifier with the primary coil 14, driven by a 20 KHZ power amplifier 15, hooked up in such a fashion as to have feedback from its output to its input causing this amplifier to form a resonate power oscillator which is continuously operating.

This air core transformer arrangement eliminates the need for a battery in the tag which would otherwise have to be replaced from time to time. Also, because the transformer efficiency is inversely proportional to the square of the distance, the transponder 1, is fully powered up when it is four (4) inches or less from the identifier 2, and will completely shut off when it is more than 12 inches away. This property helps to prevent erroneous signals from being emitted from any of the transponders when an animal is not directly in front of the feeder 4.

In FIG. 2 the printed circuit board assembly 7 contains the electronic components of Transponder 1. This assembly 7 is mounted in a cavity of a mold 8 made of plastic such as nylon, ABS plastic or polyurethane, or other material suitable for use with the electronic functions described and the harsh environment which can be encountered in use. The cavity is preferrably filled with conventional readily available black epoxy potting compound or other appropriate material to form a solid module that is hung from the animals neck on a chain or rope 3. The chain or rope 3 connects to the transponder module by two metal fasteners 9. It is also contemplated that the tag can be formed directly from inexpensive thermoplastic materials by injection molding directly around the passive tag components.

On the front of this case 8 a number can be hot stamped or otherwise imprinted or affixed to correspond with the digital code encoded within the transponder to visually identify the animal's number. The encoding can be accomplished during manufacture by cutting certain printed circuit traces 13 (FIG. 3) attached to an encoder circuit 11, in the device shown; or by any other suitable preprograming techniques available for use with other preprogramable components.

FIG. 3 is a block diagram of the transponder 1. Coil 6 picks up the electromagnetic energy from the primary 14 in the identifier 2 at approximately 20 Khz. This energy is rectified and filtered to produce a DC voltage that provides power for the passive transponder.

A free running conventional multivibrator circuit 10 provides the encoder 11 with start pulses at regular intervals, thus causing the encoder to send a digital burst of data to the RF oscillator 12 at regular intervals. This interval can typically be about one-tenth second.

The multivibrator 10 can be composed of a standard CMOS logic gate MC14011B. The encoder 11 is a device manufactured by Supertex, Inc. part number ED-9. This device is primarily used in devices used by the garage door opener industry and is manufactured in CMOS because of the low power consumption.

The RF oscillator 12 is, in this embodiment, a J-FET transistor with an approximate 3.5 Mhz crystal wired from drain to gate. This oscillator is keyed from the output of the encoder. The drain of the transistor is connected to a circuit trace on the printed circuit board 7 that acts as an antenna to radiate the energy to the receiver 16 in the identifier. The power input to the RF oscillator 12 is approximately 100 microwatts thus limiting the RF radiation to a level which in the described application does not require a license from the Federal Communications Commission.

During manufacture, the actual coding of the encoder device 11 in the transponder is done by cutting printed circuit traces 13 that are wired to the inputs of the encoder device 11. In the embodiment described, there are nine such traces giving a total combination of codes to equal 512 different codes from 0 to 511. Number 0 (zero) is typically unused because zero is the same number read if no transponder is present or can be utilized in the fail safe feature to feed a standard ration when a transponder is present but no valid number is read.

FIG. 4 is a block diagram of the identifier 2, which is mounted to the front of the feeder 4 to identify the animal that walks up and sticks her head into the feeder to be fed. In operation, the identifier supplies the energy to the transponder via the primary winding of the air core transformer 14 as previously described. The transponder 1 then transmits a 3.5 Mhz RF signal to the receiver 16 in the identifier 2 a code number programmed in the transponder. The receiver 16 converts the RF signal to a digital level, serial bit stream that is sent to a decoder circuit 16, (manufactured by Supertex, Inc. part number ED-15) which strips off the preamble and decodes the encoded signal from the transponder into a clocked data bit stream. This clocked data bit stream is sent to a shift register 17 that converts the serial data to parallel data. The decoder circuit gives a signal output called "data valid" 18 indicating that what is now in the shift register 17 is a valid block of data. The logic circuit 19 counts the valid reads, and when a predetermined number of valid reads are received, an enable signal 20 is sent to a latch which takes the parallel data and stores it. The reason the latch is necessary is that the next burst of data will be coming through almost immediately and the data in the shift register could otherwise be scrambled as data is shifted through the register. The computer can take this data and read it at random times, therefore the data must be stored in a more permanent register.

The logic block 19 also has a circuit which provides a signal called "Valid Tag" 21 that goes true so long as a transponder is continuously near the identifier. As soon as the animal leaves the feeder 4, the "Valid Tag" 21 signal goes away, signaling the system that the motor 23 should be shut off.

The main computer, not shown in the drawing can be programmed to continuously poll all of the identifiers 2 in a conventional manner. Each identifier must be assigned an individual address 22 so that the computer can individually communicate with each of the identifiers in the system. The means by which the computer communicates with these identifiers is via a 20 milliamp current loop that interconnects all of the identifiers in the system. The current loop can be a standard industrial means of communication over a pair of wires. In some applications, it may be desirable to have an isolated three or four wire current loop isolated by optical isolation for component protection from lightening strikes or line surges from other causes. It is further contemplated that standard AC line wires can be employed if it is desired not to string additional wiring. The communications format used in this embodiment is also an industrial standard called ASCII, thus allowing almost any computer to control and operate with this identification system. In addition, each identifier has its own individual address code 22, and responds back to the computer with the data 25 which it takes from the latch 17 described earlier in this text. This data containing the transponder number is transmitted back to the computer where a decision is made whether to feed the animal. If the animal is to be fed, the next time that the identifier is polled an additional bit 26 is sent along with the address giving the identifier the "OK" to turn on the motor 23. This "OK" is anded at 27 with the signal "Valid Tag" 21 if both signals are true. The output gates on a solid state relay 28 then switches power to the motor 23, which will then auger in the feed to the animal.

The motor 23 is selected to run at a constant speed and therefore the rate of feed conveyed will be essentially constant with time. Therefore, the computer can calculate the amount of feed moved to the feeder and hypothetically consumed by multiplying the pounds per second of feed the motor can deliver by the time the motor is on.

Figure 5:
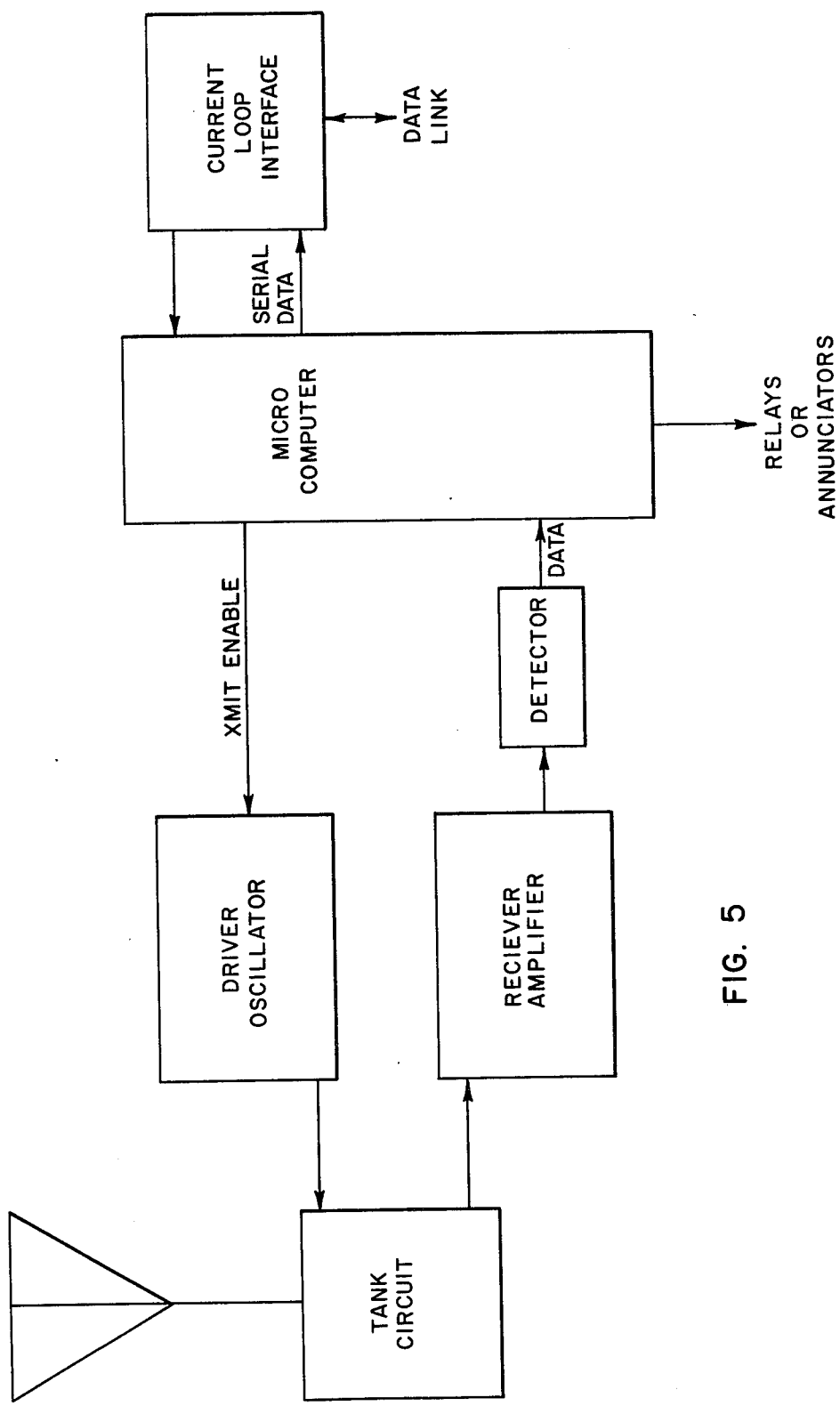
FIG. 5 is a block diagram of another embodiment of the identifier of the present invention wherein a microcomputer is used.
Figure 6:
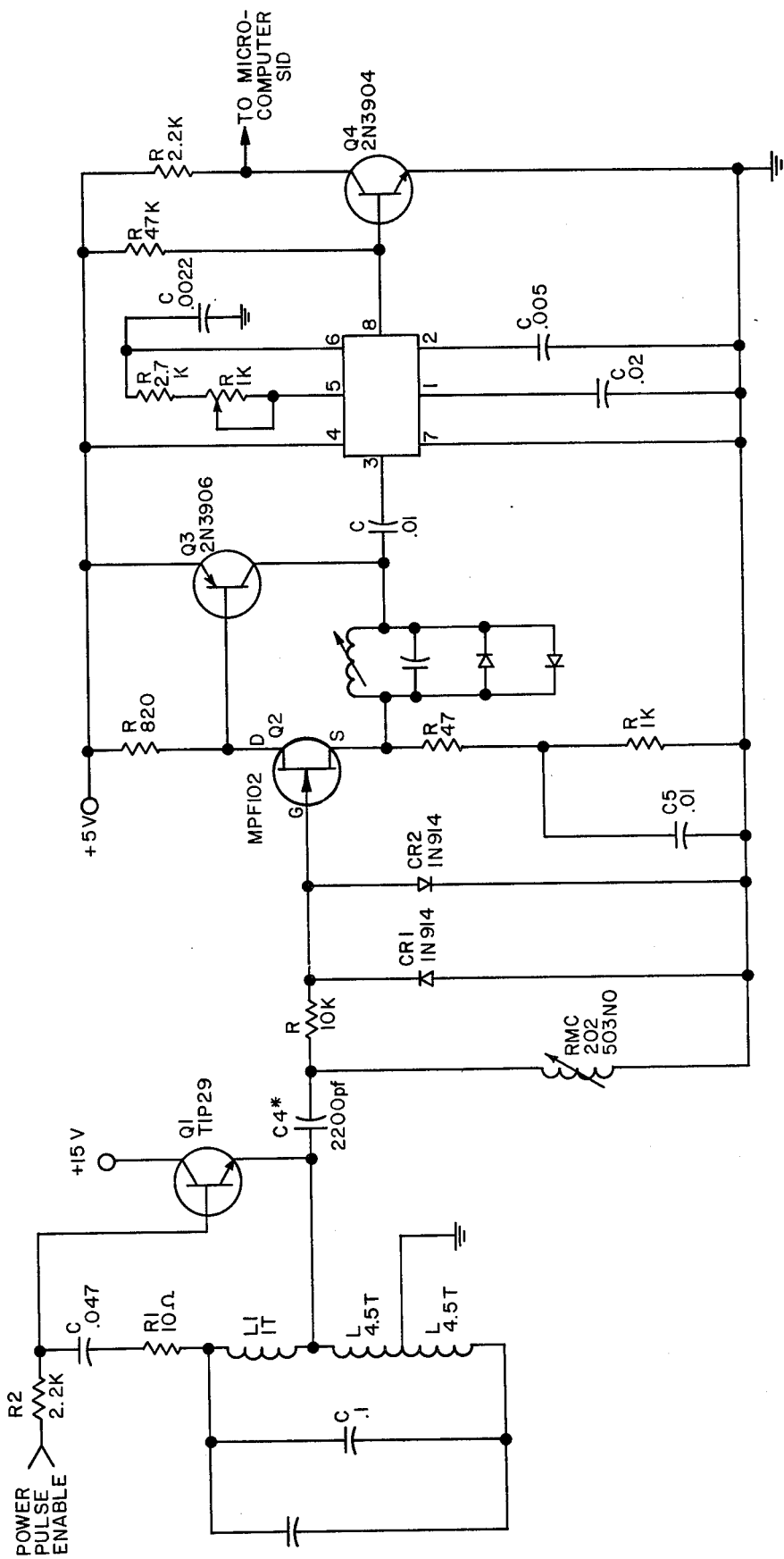
FIG. 6 is an electrical schematic drawing of a particular identifier which can be used according to FIG. 5.
Figure 7:
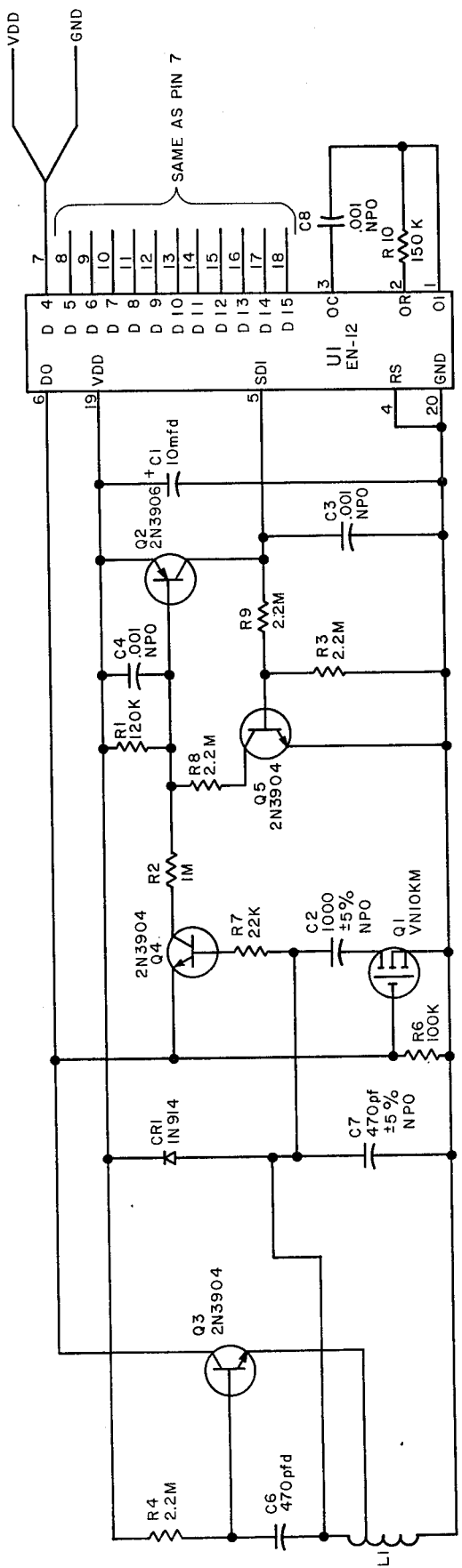
FIG. 7 is an electrical schematic of the preferred circuit utilized in the present invention for the passive embodiment of the electronic identification device described.

In yet another embodiment of this invention shown in FIGS. 5, 6 and 7, the identifier previously described is operated intermittently to both power the transponder, and between power pulses receive transmissions from the transponder in the tag. The particular transponder circuitry employed and described herein, receives the pulses and stores the energy received at one frequency and when the stored energy is sufficient to transmit the coded information to the identifier at another different frequency, this is done between the power pulses. The particular circuitry employed for these functions in both the identifier and the tag transponder, are optimized so as to provide for a greater range for the transmission and reception without any significant loss in the signal to noise ratio desired for the tag and identifier used in the dairy cattle application previously described. Indeed, the improved signal to noise ratio makes the system more suitable for other different identification functions where range is more important. Further, the use of different frequences for transmit and receive, prevents receiver interference from other identifiers that may be asynchronously transmitting power pulses in the vicinity. In addition to the foregoing, novel circuit means can be provided which extends the usefulness of the system to applications where CMOS components are used and the system requirements dictate that there be only a modest power drain. For example this circuitry can be advantageously used where the operating power is supplied by a charged capacitor or by small batteries which must have long life or are used in environments such as extreme cold where excess current drain would shorten their life.

Although the circuitry described herein can be designed to function at almost any suitable frequency the preferred embodiments are designed to transmit power from the identifier at 150–200 khz and the tag is designed to receive at the preselected frequency of transmission of the identifier and send a response at about 125 khz to the receiver of the identifier.

Referring to FIG. 7, the tag circuitry employs a CMOS encoder device EN-12 and associated circuitry for minimum power consumption. The antenna coil tank circuit L-1, C-7 receives a power pulse from the identifier (FIG. 6) which is rectified by the diode CR-1 and begins to charge the capacitor C-1. Upon the termination of the power pulse from the oscillator in the identifier, the capacitor C-1, if sufficiently charged will provide a signal to initiate a start pulse at transistor Q-2. This initiating process begins if the voltage of C-1 has reached a threshold value of 3.5 volts. The typical duration of the power burst will be about 200–800 milliseconds thereby providing a sufficient pause between bursts to enable the subsequent digital data transmission functions to be accomplished.

The range of the identifier from the tag will be dependent upon several factors. The most important factor is of course the ability of C-1 to receive and store sufficient energy to initiate the start pulse at the end of any transmitted power burst from the identifier. Typically, sufficient energy can be received and stored for the tag to transmit the desired information at a distance of from about two to three feet or one meter. A short delay in the transmission from the tag is provided by the internal time constant provided by the C3-R3 network. This delay in the preferred embodiment, should be between 80–150 milliseconds.

After such delay, the start pulse impressed on SDI of the EN-12 turns on power to the encoder and transmitter circuitry and to MOS Field Effect Transistor Q1 which switches in the additional tank circuit capacitor C2. This changes the resonant frequency of the antenna coil Tank circuit L-1, C-2, C-7 to the preselected transmitting frequency; which in the described embodiment is 125 khz. The oscillator Q-3 generates a carrier frequency which is keyed on and off by the data output from the digital encoder circuit, terminal CMOS EN-12, at the terminal DO thereof. In order to filter out unwanted parasitic oscillations which might accompany this output, a capacitor C-4 is provided as shown, which limits undesired switching of Q-2. In addition to the foregoing, the circuit including Q-5 is provided with circuitry which operates as a modified Schmitt trigger which prevents excessive current draw by the CMOS EN-12 and insures that full voltage is applied to the SDI input thereby preventing excessive power consumption at less than the optimum gate input voltage. The internal coding of the CMOS EN-12 is provided by interrupting either the VDD or ground connection from the terminals D4 through D15. The circuit connected to terminals OC and OR establishes the clocking rate of the digital data transmission.

The foregoing description of the passive version of the transponder of the present invention can be modified to perform the same data transmission functions as an active tag. That is, a battery may be substituted for the capacitor C-1, and the resistance of R1 can be adjusted to 180 K. In such a configuration, the identifier need only contain a sensitive receiver for the frequency broadcast in order for the identification or other function to be accomplished. The advantage of such a substitution would be in the greater range that the tag would have since the proximity to the identifier for the reception of power bursts would be reduced and the range would depend primarily on the sensitivity of the receiver. There would of course be the attendant drawback that batteries would have to be replaced from time to time. In applications where that would not be a serious drawback, such as security, access control, or hospital or other like kinds of environments, such a device would be useful.

The identifier utilized with the passive (non-battery) tag transponder previously described, may be alternatively provided with a microcomputer, such as the Intel 8085 or 8051. Briefly, the identifier consists of circuitry to perform the functions shown in the block diagrams shown in FIG. 5. In sequence, the power burst at one frequency is provided by the driver oscillator and the duration of the burst is governed by the transmit enable command from the microprocessor. L-1 of the identifier using the circuitry shown in FIG. 6 alternates between sending pulses of energy and receiving information from the transponder. The bandwidth or "Q" of the tank circuit is broad enough to permit both transmission and reception on separate frequencies without change in tuning. When the identifier is in the receive mode, if any signal is received from the transponder tag, it is amplified in a conventional manner and then detected and reduced to a digital pulse train for input into the microprocessor.

The microcomputer sets the time for sending and receiving, typically, when a 5 volt signal is impressed on R-2 the driver oscillator transmits the requisite power pulse.

Referring specifically to FIG. 6, the driver oscillator circuit, which includes Q-1, transmits the 150–200 Khz signal previously described. The tuned circuit including C-4 and R-1, receives the 125 Khz signal sent by the tag/transponder. That signal is amplified by the feedback amplifier circuit, including Q-2 and Q-3. The amplified signal is then detected. Before amplification the 125 Khz signal is also connected to ground through two diodes CR 1 and CR 2 in order to remove spurious or unwanted signals that might otherwise be amplified. A software algorithm (further described hereinafter) decodes the digital pulse train into meaningful data or if none is present, it reenables the driver oscillator in the same manner as would be done if data were present. A proper software algorithm for use in the present invention will be capable of decoding the data received form the tag transponder in spite of wide variations in the rate of data transmission. The data is then fed to another data processing station, which can be a central computer having the proper interface and, in the case of the dairy cattle application, the herd information, as well as being provided with appropriate software for its processing of the stored and received data. It is also contemplated that a storage and/or processing station could be provided either at the site of the identifier or elsewhere, that would enable some functions of the central computer to be performed independently, as well as having the capability of interacting in a predetermined manner with the central computer. In other words, it is envisioned that almost any mode for the handling the data transmitted should be suitable for use with the tag and identifier of the present invention.

After the processing of the data, however accomplished, the commands for activating any predetermined function, such as dispensing feed or the like, can be sent to the microprocessor and the commanded function performed. In this manner the microprocessor can activate motor relays or other controls or indicators according to predetermined instructions. As stated previously, these instructions are or can be sent to the identifier via three or four wire current loop or other appropriate connection.

In operation, the identifier can power a passive tag with more than one power burst depending on the application, range or specific circuit requirements.

It is also contemplated as a feature of this invention that when several timed power bursts are required to energize a particular tag circuit configuration, that the time required for the tag to respond could be measured and an estimate of the distance of the tag from the identifier could be made. It is also contemplated that variations in the strength of the power burst can be provided in response to such estimate to accomplish specific different functions than specifically described herein. That is, either stronger or weaker bursts could be provided for specific applications. Where it is desirable to increase the range of the system, i.e. provide for accurate identification with distances between the tag and identifier greater than one meter, the magnitude of the power burst and even its duration can be increased to provide the required results.

The particular microcomputer used in this description is characterized as having the following specified functions:
(1) 8-bit
(2) 6.144 MHz clock rate
(3) integral UART
(4) 4K bytes of ROM
(5) 128 or 256 bytes of RAM
(6) 48-bit or 32-bit bi-directional I/O ports Since the microcomputer used is capable of being programmed, it can contain predetermined internal algorithms to accomplish a number of separate functions including:
(1) transmitter-receiver control
(2) Tag data decoding
(3) Sending and receiving system serial data (UART)
(4) Operating external relays, signal lines or annunciators
(5) Reading A/D converter inputs
(6) Reading certain switch inputs
(7) Counting pulses on an input pulse stream. (milk monitoring)

In one version of the preferred embodiment, the microcomputer uses a special group of "mode select" input lines to assign its own "personality" suitable to a given application (i.e. feeder, parlor ID, alleyway ID, alarm, etc.). It thereby makes use of whatever subset of the above software functions may be necessary for that specific application. These mode select input lines can be hard-wired when the microcomputer IC(s) is (are) installed in a particular application-specific printed circuit board.

FEEDER PROGRAM

Figure 8:
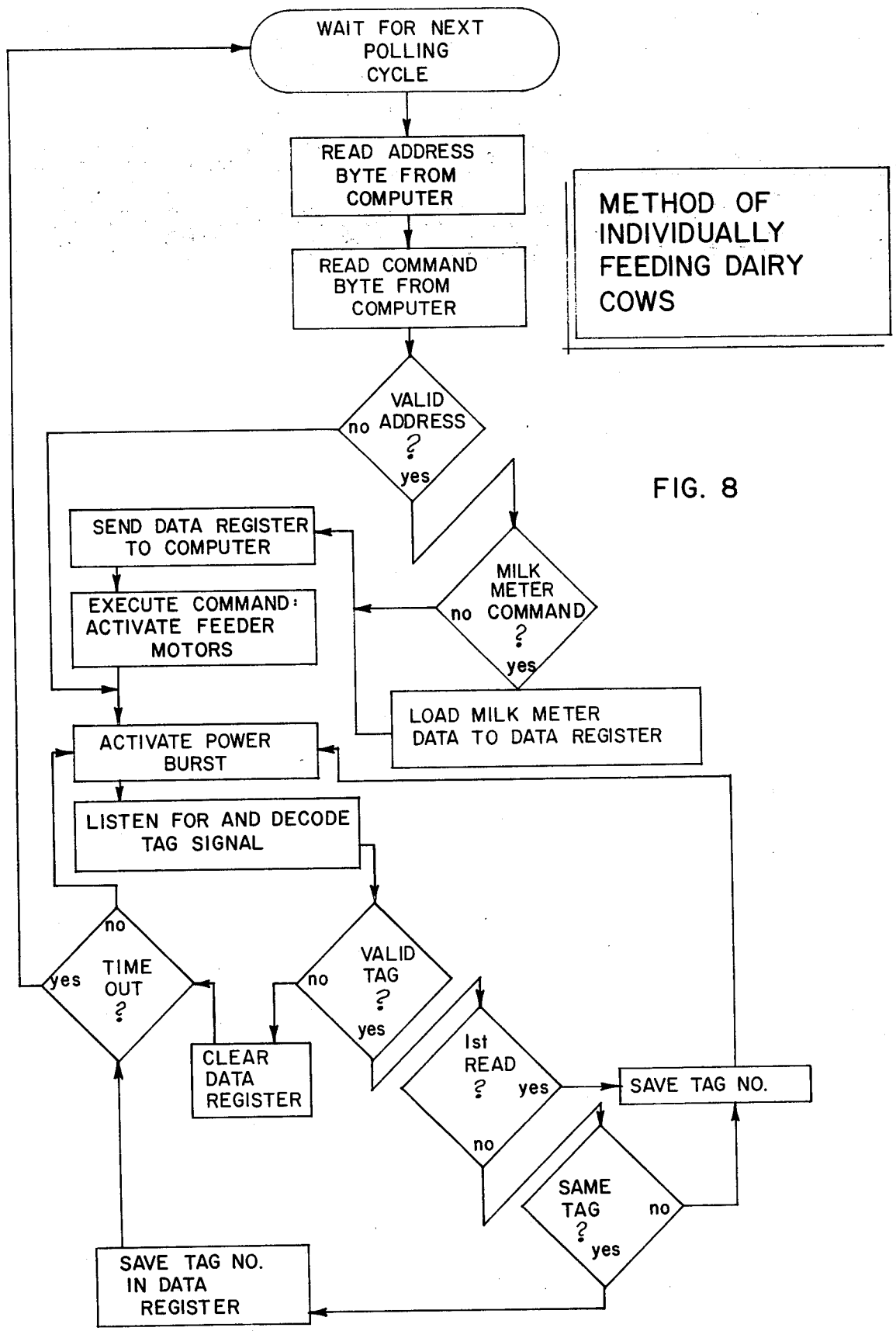
FIGS. 8-10 are flow charts of software programs that could be used by a computer in practicing the present invention.

The flow chart for the feeder program is shown in FIG. 8. The identifier microcomputer software serves primarily to decode tag signals and to communicate with the central computer. During each polling cycle (1/16 second), the microcomputer receives a two byte polling message from the central computer consisting of an address byte and a command byte. If the message is not addressed to the particular feeder, the message is ignored and the program proceeds to look for tags. If however, the message is addressed to the particular feeder, the program proceeds to execute the command. If the command is to read milk meter data, such data is then stored in the data register for transmission back to the central computer. If the command is for identifying tag data, the contents of the data register are not altered and remain to be transmitted. The program then proceeds to send a power burst which will elicit a response from any nearby tag and then attempt to decode the response signal. When a valid tag has been decoded two or more times in succession, the tag number is then stored in the data register for subsequent transmission to the central computer on the next polling cycle.

CENTRAL COMPUTER PROCESSING

Central computer data acquisition, processing and feeder control in the present unit comprise: polling each of up to 16 identifier/feeder units once per second, receiving identification or other (e.g. milkmeter) data back from each identifier associated with a particular feeder unit once per second, calculating the latest total amount fed each cow, comparing such total with daily allocations, and sending motor-on or motor-off or other commands to each identifier/feeder unit.

Data processing is carried out by a microcomputer system capable of interrupt software operation including foreground to background processing and the like. Operator interface functions (i.e. keyboard, display, etc.) and data management functions (printed reports, etc.) are performed by a foreground program which normally operates continuously on a 24 hour basis. This foreground program allows the dairyman to at any time, store in memory and display on command, data on each of his feeders.

The kinds of data could include such things as the number of visits to a particular feeder and by which cows, the feed rate and current functionality of the feeder. Also, the feeding status of the herd can be stored and displayed including such information as the preselected feed allocation for each cow, the total feed consumed, monthly totals and current status that day.

INTERRUPT 7.5 BACKGROUND PROGRAM

Figure 9:
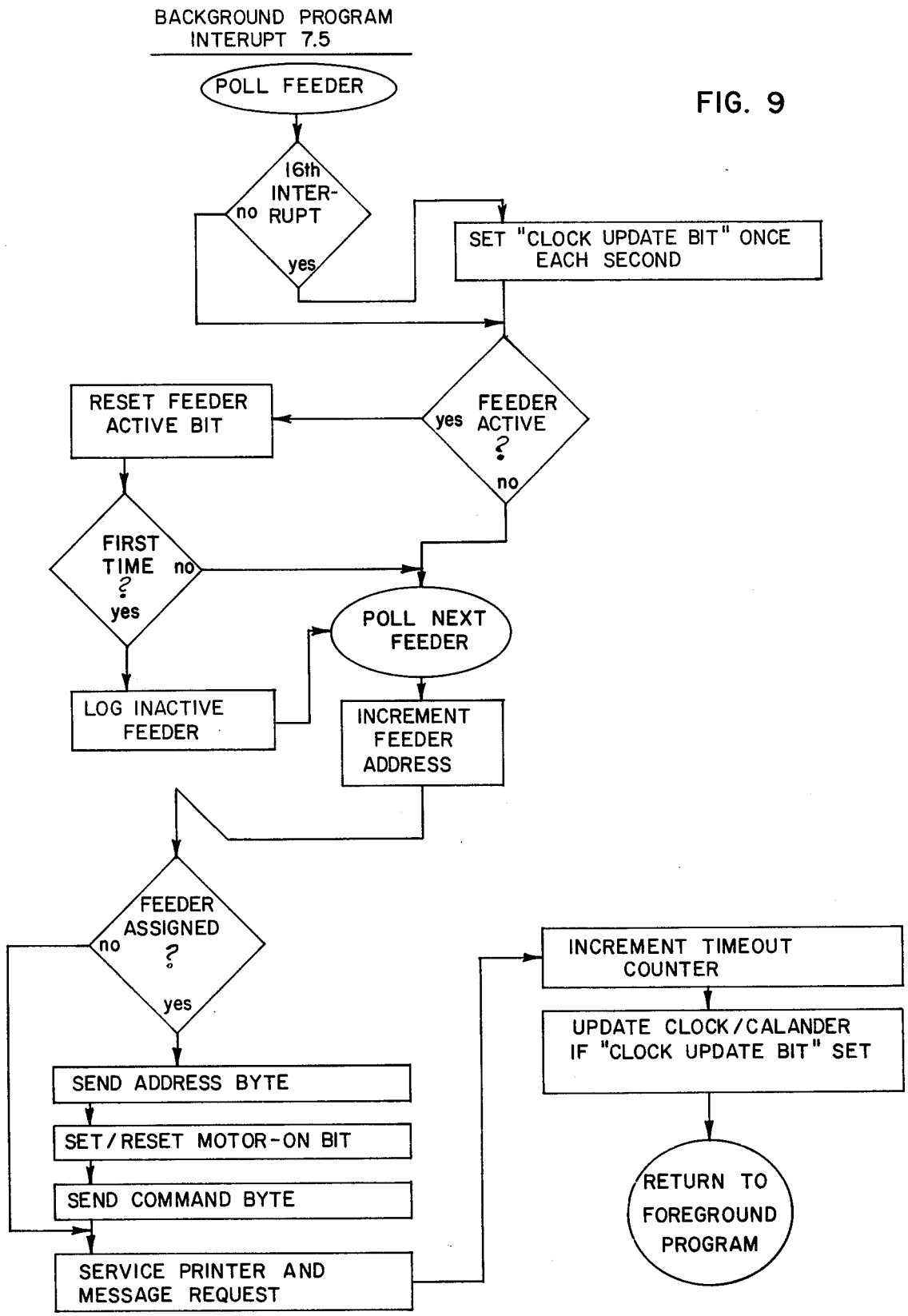

As shown in FIG. 9, real-time feeder communication and control functions are performed by a background software program running in an interrupt mode.

Every 1/16 of a second, a signal is generated by the timer counter of the central computer. This signal initiates the so-called 7.5 interrupt program which then polls the next feeder in the polling sequence.

During this sequence, another program is used to determine whether any feeder is registering an activity or response.

If no response had been received to the previous feeder poll, a feeder inactive message is logged for future access. The poll consists of a two byte transmission; an address byte specifying the feeder and a command byte specifying the feeder response desired or other feeder action such as turning on or off feed dispensing motors. The message bytes are transmitted in standard ASCII format at 1200 baud in full duplex. The interrupt 7.5 background program also updates the calendar/clock each second and manages data output to a logging printer.

INTERRUPT 6.5 BACKGROUND PROGRAM

Figure 10:
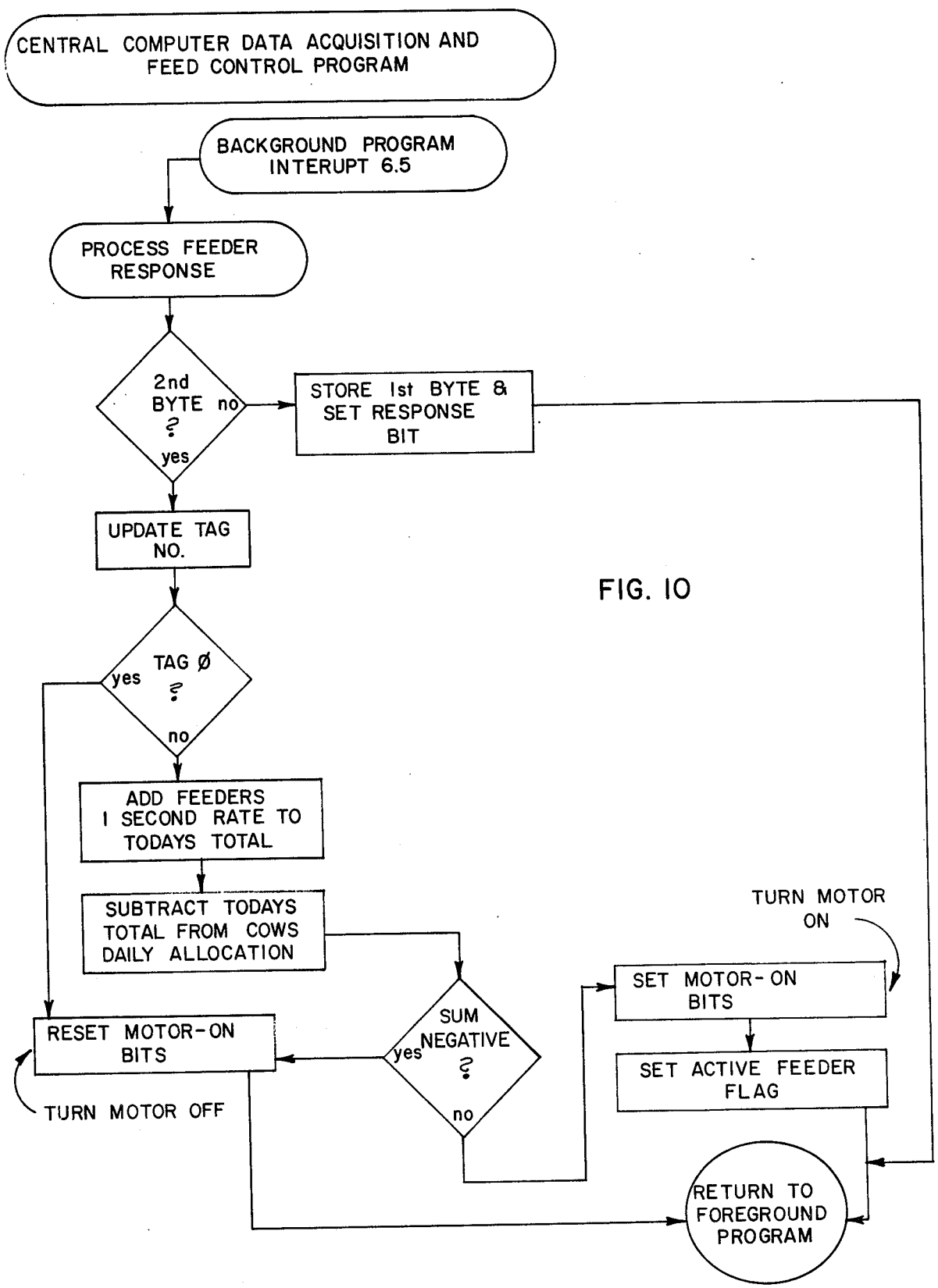

Referring to FIG. 10, when each identifier receives the previously described poll message, it compares the address byte for its own specific address. If the address matches, the feeder sends a two byte response message back to the central computer. Upon arrival at the central computer, each byte of this message generates an interrupt signal which initiates the interrupt 6.5 background program which serves to receive and process the feeder response message. This routine merely receives and stores the first byte. When the second byte arrives, it proceeds to process the entire message. If a tag zero message is received from the feeder, this indicates that no cow is at the feeder and that the motor-on bits should be reset for transmission to the feeder on the next polling cycle. If the tag message indicates any number other than zero, the record for that tag is then looked up in the computers data memory. The running feed total for the particular cow is then increased by the amount of feed dispensed each second. The resulting new total is then compared to the cows stored maximum feed allocation. If the total is greater, the cow has exceeded her allotment and the motor-on bits are reset for later transmission to the feeder by the polling program. If the cow has not exceeded her allotment, the motors are turned on and feed is dispensed to the cow.

What is claimed is:

1. A passive identification system comprising:
    means for generating an electromagnetic field, containing circuit means comprising:
        a power supply; and
        a self-resonating power supply oscillator electrically connected to said power supply; and
        a first coil electrically connected to said power oscillator wherein said power supply activates said self-resonating oscillator for a first time interval, during which first time interval said self-resonating oscillator drives said coil at a first frequency;
    a plurality of means for transmitting radio frequency radiation separate and spaced from said generating means each including:
        a second coil for receiving electrical energy from said generating means at a position remote therefrom; and
        means powered by said second coil for encoding a digital signal and transmitting through said second coil the encoded signal at a second frequency different from said first frequency during a second time interval different from said first time interval, said generating means not delivering electrical energy to said coil means during said second timer interval; and
    receiving means remote from said transmitting means for receiving the transmitted encoded signal; and
    decoding means; and
    comparison means electrically connected to said decoding means and including means for storage of digital data and for comparing the received decoded signal with stored data to identify the specific transmitting means whose signal has been received and compared.

2. The passive identification system of claim 1 wherein said second coil in each of said transmitting means includes circuit means including:
    a receiving coil for receiving a portion of the electromagnetic energy radiated by said generating means during said first time interval, electrically connected through rectifier means to storage means for storing the energy received until a predetermined signal voltage is reached, whereupon the encoding means is capable of transmitting the encoded signal at said second frequency.

3. The passive identification system of claim 2 wherein said generating means generates electromagnetic energy at a frequency of greater than 125 Khz.

4. The passive identification system of claim 3 wherein said transmitting means transmits radio frequency radiation at 125 Khz and less.

5. The passive identification system of claim 2 wherein the receiving means utilizes the same power supply as said generating means.

6. A method of article identification comprising the steps of:
    providing the article with first means for receiving and storing a burst of electromagnetic energy through an antenna circuit and for transmitting through the same antenna circuit, at a time interval subsequent to the receipt of said burst of electromagnetic energy, a radio frequency signal modulated with a digital encoded signal representative of the identity of the article; and
    providing at a location remote from the article second means for transmitting the burst of electromagnetic energy and for receiving the modulated radio frequency radiation, said second means including decoding means for decoding the received encoded digital signal; and comparison means, including storage means for storing the digital data indicative of identity and display means electrically connected to the decoding means, for comparing the decoded signal with the stored data and indicating identity; and
    bringing the first means and the second means into close enough proximity to enable said first means to receive the burst of electromagnetic energy transmitted by said second means and to enable said second means to receive the encoded signal transmitted by said first means and identify the article bearing the first means.

7. The method of claim 6 wherein the article is ambulatory and the first means provided to said ambulatory article comprises a passive tag that is placed on or worn by said ambulatory article.

8. The method of claim 7 further including the step of providing responsive means coupled to said second means for effectuating a desired action in response to identifying the ambulatory article bearing the first means.

9. The method of claim 8 wherein the ambulatory article comprises an animal, and the desired action comprises dispensing a predetermined amount of feed for the particular animal that is identified.

10. A method of feeding animals comprising the steps of:
    providing the animal with an attached intermittent single frequency signal transmitting device capable of transmitting a data encoded digital signal indicative of the identify of the animal through a single antenna circuit embodied within said device, said device also being capable of receiving a burst of electromagnetic energy through said single antenna circuit for providing power for said device;
    providing a feeder equipped with feed dispensing means, said feeder having signal receiving and decoding means associated therewith;
    generating said burst of electromagnetic energy whenever the animal comes in close proximity to the feeder, whereby the device responds by transmitting the encoded signal;

receiving the encoded signal transmitted by the transmitting device within the signal receiving means;

decoding the received signal with said decoding means;

comparing the decoded signal with predetermined identification data in a computer to produce a signal indicative of identity and predetermined feed amount; and dispensing the predetermined feed amount to the feeder in response to the signal generated by the computer.

11. A tag or other device for use in an identification system comprising:

means for receiving a burst of electromagnetic radiation through a single antenna circuit from a source remote from said tag to provide power for the other functions of said tag;

means for transmitting radio frequency radiation through said same single antenna circuit at a frequency different from said burst of electromagnetic radiation, said radio frequency radiation being transmitted subsequent to the receipt of said electromagnetic radiation burst, and said radio frequency radiation being capable of being received at a point remote from said tag; and means for providing digital encoded information in said tag, said digital encoded means being electrically powered by the received electromagnetic radiation and being used to modulate said radio frequency radiation that is transmitted to a receiver external of said tag.

12. An identification system for uniquely identifying a plurality of objects comprising identifier circuit means for transmitting and receiving bursts of first and second signals, respectively, at first and second frequencies, respectively, through a single antenna tank circuit;

a portable transponder unit comprising single antenna circuit means for receiving said first signal burst at said first frequency or for transmitting said second signal burst at said second frequency, start circuit means for generating a start signal in response to reception of said first signal through said antenna circuit means, encoding means for generating a pre-programmed coded signal in response to said start signal, modulation means for generating said second signal at said second frequency, and for modulating said second signal with said pre-programmed coded digital signal, and for presenting said modulated second signal to said antenna circuit means;

said identifier circuit means including control means for generating said first signal and for delivering a burst of said first signal to said antenna tank circuit only at desired times and for desired durations;

decoding means for generating a decoded signal from the second signal received through said antenna tank circuit, said decoded signal being relatable to said pre-programmed coded signal of said transponder unit's encoding means, and storage means coupled to said decoding means for storing and holding said decoded signal;

whereby said decoded signal may be used to uniquely identify an object to which said portable transponder unit is attached when said transponder unit is pre-programmed with a unique identifying coded signal.

13. The identification system of claim 12 wherein said identifier means further comprises comparison means for electronically comparing the decoded signal against a plurality of stored signals in order to identify the specific transponder unit from which the decoded signal was derived; and response means for generating a plurality of control signals in response to the identification made by said comparison means; and undertaking a predetermined activity in response to said control signals.

14. The identification system of claim 12 wherein said portable transponder unit further comprises delay means for delaying the delivery of start signal to said encoding means for a pre-determined time, whereby the transmission of the modulated second signal back to the identifier circuit means may be delayed until after the transmission of said first signal to said transponder unit.

15. The identification system of claim 14 wherein the antenna circuit means of said portable transponder unit includes automatic tuning means for tuning the antenna circuit means to said first frequency when said first signal is being transmitted to said transponder unit, and for tuning the antenna circuit means to said second frequency when said second signal is being transmitted from said transponder unit.

16. The identification system of claim 15 wherein said first signal is an electromagnetic signal and wherein said portable transponder unit is a passive device that derives its operating power from the electromagnetic energy associated with said first signal.

17. The identification system of claim 16 wherein the start circuit means of said portable transponder unit includes means for storing the energy derived from said first signal, and means for detecting when said stored energy exceeds a specified threshold level, said start signal being generated when said threshold level is exceeded.

18. The identification system of claim 17 wherein said modulation means of said portable transponder unit includes an oscillator that generates a signal at said second frequency that is keyed on and off by said pre-programmed coded signal.

* * * * *